US009068810B2

(12) United States Patent
Murakawa et al.

(10) Patent No.: US 9,068,810 B2
(45) Date of Patent: Jun. 30, 2015

(54) TRUNK AREA DIMENSION MEASUREMENT DEVICE AND BODY FAT MEASUREMENT DEVICE

(75) Inventors: Yasuaki Murakawa, Kyoto (JP); Kazuhisa Tanabe, Kyoto (JP); Takehiro Hamaguchi, Kyoto (JP); Shinichi Ito, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 51 days.

(21) Appl. No.: 13/980,691

(22) PCT Filed: Nov. 22, 2011

(86) PCT No.: PCT/JP2011/076929
§ 371 (c)(1),
(2), (4) Date: Jul. 19, 2013

(87) PCT Pub. No.: WO2012/111210
PCT Pub. Date: Aug. 23, 2012

(65) Prior Publication Data
US 2013/0301060 A1    Nov. 14, 2013

(30) Foreign Application Priority Data
Feb. 18, 2011    (JP) .................................. 2011-033258

(51) Int. Cl.
*G01B 11/28*    (2006.01)
*G01B 11/06*    (2006.01)
(Continued)

(52) U.S. Cl.
CPC ................ *G01B 5/02* (2013.01); *A61B 5/0537* (2013.01); *A61B 5/1075* (2013.01);
(Continued)

(58) Field of Classification Search
USPC ................. 356/627, 628, 631, 635, 620, 622; 600/547, 414, 421, 390
See application file for complete search history.

(56) References Cited

U.S. PATENT DOCUMENTS

| 7,051,447 B2* | 5/2006 | Kikuchi et al. ................. 33/503 |
| 2006/0025701 A1* | 2/2006 | Kasahara ...................... 600/547 |
| 2011/0137198 A1 | 6/2011 | Hamaguchi et al. |
| 2011/0295144 A1* | 12/2011 | Murakawa et al. ........... 600/547 |

FOREIGN PATENT DOCUMENTS

| JP | A-1-98910 | 4/1989 |
| JP | A-2001-212111 | 8/2001 |

(Continued)

OTHER PUBLICATIONS

Jan. 10, 2012 International Search Report issued in International Application No. PCT/JP2011/076929 (with translation).

*Primary Examiner* — Rebecca C Bryant
(74) *Attorney, Agent, or Firm* — Oliff PLC

(57) ABSTRACT

The trunk area dimension measurement device includes a light reflection portion to be placed at a position of a navel of the measurement subject, a contact portion to be placed on a side surface of the measurement subject's trunk area, a support column having a contact detection unit that detects the contact with the contact portion and that extends in the vertical direction, a measurement bar that is supported pivotably about a first support point vertically with respect to the support column and that extends above the measurement subject's trunk area, an optical sensor that is held by the measurement bar positioned above the measurement subject's trunk area and that is held pivotably about a second support point so as to hang down in a gravity direction, and an angle sensor that is provided at either one of the first support point and the second support point.

8 Claims, 4 Drawing Sheets

(51) Int. Cl.
    *G01B 5/02*     (2006.01)
    *A61B 5/053*    (2006.01)
    *A61B 5/107*    (2006.01)
    *A61B 5/00*     (2006.01)
    *G01B 11/04*    (2006.01)

(52) U.S. Cl.
    CPC ............ *A61B 5/1079* (2013.01); *A61B 5/4872* (2013.01); *G01B 11/043* (2013.01); *A61B 5/6829* (2013.01); *A61B 5/6823* (2013.01); *A61B 5/6825* (2013.01)

(56) References Cited

FOREIGN PATENT DOCUMENTS

| | | |
|---|---|---|
| JP | A-2005-288023 | 10/2005 |
| JP | A-2008-23232 | 2/2008 |
| JP | A-2008-237571 | 10/2008 |
| JP | A-2009-22482 | 2/2009 |
| JP | A-2010-69250 | 4/2010 |
| WO | WO 2010/032837 A1 | 3/2010 |

* cited by examiner

TRUNK AREA DIMENSION MEASUREMENT DEVICE AND BODY FAT MEASUREMENT DEVICE

TECHNICAL FIELD

The present invention relates to a trunk area dimension measurement device for measuring a trunk area width and a trunk area depth of a measurement subject and a body fat measurement device employing the trunk area dimension measurement device.

BACKGROUND ART

In recent years, body fat mass is gaining attention as an indicator used to determine the health of a measurement subject. In particular, visceral fat mass is gaining attention as an indicator for determining whether or not a person is suffering from central obesity. Central obesity is said to bring about lifestyle-related diseases that can easily lead to artery hardening, such as diabetes, hypertension, and hyperlipidemia, and the stated indicators hold promise in terms of preventing such diseases. "Visceral fat" refers to fat that accumulates around the internal organs on the inner side of the abdominal muscles and the back muscles, and is distinct from the subcutaneous fat that is located toward the surface of the trunk area. It is typical to employ the area occupied by visceral fat in a cross-section of the trunk area that corresponds to the navel (referred to as a "visceral fat cross-sectional area" hereinafter) as an indicator of the visceral fat mass.

Image Analysis Technique

Normally, visceral fat mass is measured by analyzing images obtained through X-ray computed tomography (CT), magnetic resonance imaging (MRI), or the like. In such image analysis, the visceral fat cross-sectional area is calculated geometrically from a tomographic image of the trunk area obtained by using X-ray CT, MRI, or the like. However, it is necessary to use several pieces of large equipment installed in a medical facility, such as X-ray CT, MRI, or other machines, in order to make use of such a measurement method; thus it is extremely difficult to measure visceral fat mass on a daily basis through such a measurement method. X-ray CT also poses the problem of exposure to radiation, and thus cannot necessarily be called a desirable measurement method.

Body Impedance Technique

A body impedance technique is being considered as an alternative to these measurement methods. The body impedance technique is a method for measuring body fat mass widely used in household-based body fat measurement devices; in this technique, electrodes are placed in contact with the four limbs, the body impedance is measured using those electrodes, and the body fat mass is calculated from the measured body impedance. The stated household body fat measurement device makes it possible to accurately measure the extent of body fat buildup throughout the entire body or in specific areas such as the four limbs, the trunk area, or the like.

To make it possible to measure the visceral fat mass, subcutaneous fat mass, and so on with a high degree of accuracy using the stated body impedance, it is necessary to measure the measurement subject's trunk area body build, such as the trunk area width and the trunk area depth, and use the measurements in computation processes for calculating the body fat mass. Devices for measuring the measurement subject's trunk area body build are disclosed in JP 2005-288023A (Patent Literature 1), JP 2008-23232A (Patent Literature 2), JP 2008-237571A (Patent Literature 3), JP 2009-22482A (Patent Literature 4), and JP 2010-69250A (Patent Literature 5).

CITATION LIST

Patent Literature

Patent Literature 1: JP 2005-288023A
Patent Literature 2: JP 2008-23232A
Patent Literature 3: JP 2008-237571A
Patent Literature 4: JP 2009-22482A
Patent Literature 5: JP 2010-69250A

SUMMARY OF INVENTION

Technical Problem

The measurement devices for measuring the measurement subject's trunk area body build disclosed in the above-mentioned literatures are large-scaled devices that surround the circumference of the measurement subject's trunk area, and require a large space for installing and accommodating the measurement devices when used in a household. Moreover, since the measurement devices have many operating units and the internal structure thereof is relatively complicated, there is a concern in that the cost of the measurement devices increases.

Having been achieved in order to solve the stated problems, it is an object of the present invention to provide a trunk area dimension measurement device that is not large-scaled, has a simple structure, and also has a configuration that is capable of suppressing an increase in the cost, and to provide a body fat measurement device employing the trunk area dimension measurement device.

Solution to Problem

A trunk area dimension measurement device according to the present invention is a trunk area dimension measurement device for measuring a trunk area width and a trunk are depth of a measurement subject who is lying face-up, including: a support column to be placed on a side surface of the trunk area of the measurement subject; a measurement bar that is supported pivotably about a first support point vertically with respect to the support column and that extends above the trunk area of the measurement subject; a distance sensor that is held by the measurement bar positioned above the trunk area of the measurement subject and that is held pivotably about a second support point so as to hang down in a gravity direction; an angle sensor that is provided at either one of the first support point and the second support point; and a control unit that processes information on an inclination angle of the measurement bar with respect to a vertical direction that is obtained from the angle sensor and information that is obtained from the distance sensor.

The control unit measures the trunk area width and the trunk area depth of the measurement subject based on distance information obtained based on the information obtained from the distance sensor and the inclination angle information of the measurement bar with respect to the vertical direction that is obtained from the angle sensor.

According to another form, the trunk area dimension measurement device further includes: a light reflection portion to be placed at a position of a navel of the measurement subject; and a contact detection unit that is provided on the support column and that detects contact with the trunk area, wherein an optical sensor is used as the distance sensor, and when measuring the trunk area width and the trunk area depth of the measurement subject, the control unit obtains information on the contact with the trunk area from the contact detection unit and measures the trunk area width and the trunk area depth of the measurement subject, based on information on a distance between the optical sensor and the light reflection portion obtained based on the information obtained from the optical sensor in a state in which light emitted from the optical sensor is reflected at the light reflection portion and returns to the optical sensor and the inclination angle information of the measurement bar with respect to the vertical direction that is obtained from the angle sensor.

According to another form, a contact portion is placed on one side surface of the measurement subject's trunk area, and the contact detection unit sends: information of a current flow to the control unit when the contact portion is in contact with the contact detection unit, and information of no current flow to the control unit when the contact portion is not in contact with the contact detection unit.

According to another form, the light reflection portion and the contact portion are provided on a belt member to be fitted around the trunk area of the measurement subject.

According to another form, the trunk area dimension measurement device has a grip portion on a side opposite to the side on which the optical sensor is provided with the first support point of the measurement bar interposed therebetween, wherein a measurement start switch that sends a signal for starting a measurement performed by the trunk area dimension measurement device to the control unit is provided in the vicinity of the grip portion.

A body fat measurement device according to the present invention includes any of the stated trunk area dimension measurement devices.

Advantageous Effects of Invention

According to the present invention, it is possible to provide a trunk area dimension measurement device that is not large-scaled, has a simple structure, and also has a configuration that is capable of suppressing an increase in the cost, and to provide a body fat measurement device employing the trunk area dimension measurement device.

DESCRIPTION OF EMBODIMENTS

Figure 1A:
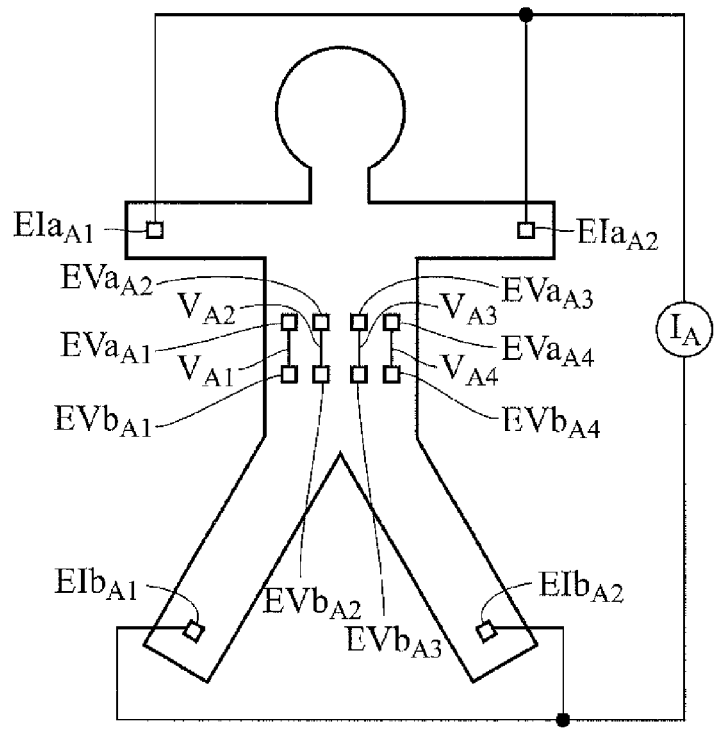
FIG. 1A and FIG. 1B are diagrams illustrating the fundamentals of measurement performed by a body fat measurement device according to an embodiment of the present invention.

Hereinafter, a trunk area dimension measurement device and a body fat measurement device according to embodiments of the present invention will be described in detail with reference to the drawings. When numbers, amounts, and so on are discussed in the following embodiments, unless explicitly mentioned otherwise, the scope of the present invention is not necessarily limited to those numbers, amounts, and so on. Moreover, identical and corresponding components may be assigned identical reference numerals, and redundant descriptions thereof may be omitted.

Before describing the various embodiments of the present invention, definitions will first be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Meanwhile, "body axis" refers to an axis located along the direction in which the trunk area extends, or in other words, an axis extending in a direction approximately perpendicular to a side cross-section of the measurement subject's trunk area.

Figure 1B:
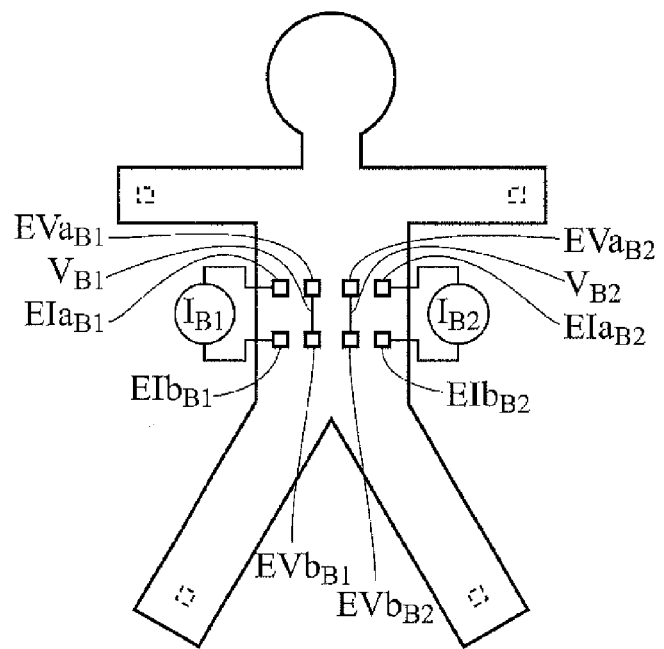

FIG. 1A and FIG. 1B are diagrams illustrating the fundamentals of measurement performed by a body fat measurement device according to an embodiment of the present invention. Here, FIG. 1A is a diagram illustrating the placement of electrodes when obtaining a body impedance for the entire trunk area, whereas FIG. 1B is a diagram illustrating the placement of electrodes when obtaining a body impedance for a surface layer area on the back area side of the trunk area. First, the fundamentals of measurement performed by the body fat measurement device according to the present embodiment will be described with reference to FIG. 1A and FIG. 1B. Note that FIG. 1A and FIG. 1B both illustrate the measurement subject from the back side thereof.

Fundamentals of Measurement Performed by Body Fat Measurement Device

As shown in FIG. 1A, electrodes $EIa_{A1}$ and $EIa_{A2}$ are attached to the surface of the left arm of the measurement subject and the surface of the right arm of the measurement subject, respectively, in order to obtain the body impedance for the entire trunk area. Likewise, electrodes $EIb_{A1}$ and $EIb_{A2}$ are attached to the surface of the left leg of the measurement subject and the surface of the right leg of the measurement subject, respectively. Four pairs of electrodes are attached to the back area surface of the measurement subject, with each pair disposed so as to follow the body axis direction, and with the four pairs arranged in the widthwise direction of the trunk area. In other words, as shown in FIG. 1A a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

In this state, a constant current IA that passes through the trunk area is applied to the measurement subject using the electrodes $EIa_m$, $EIa_{A2}$, $EIb_{A1}$, and $EIb_{A2}$ attached to both arms and both legs, respectively. While the constant current IA is applied, a potential difference $V_{A1}$ is detected using the pair of electrodes $EVa_{A1}$ and $EVb_{A1}$ attached to the back area surface, a potential difference $V_{A2}$ is detected using the pair of electrodes $EVa_{A2}$ and $EVb_{A2}$ attached to the back area surface, a potential difference $V_{A3}$ is detected using the pair of electrodes $EVa_{A3}$ and $EVb_{A3}$ attached to the back area surface, and a potential difference $V_{A4}$ is detected using the pair of electrodes $EVa_{A4}$ and $EVb_{A4}$ attached to the back area surface.

A body impedance Zt of the entire trunk area is calculated from the potential differences $V_{A1}$, $V_{A2}$, $V_{A3}$, and $V_{A4}$ detected in this manner. Note that if the body impedance Zt is found at this time by calculating the average value of the four stated potential differences $V_{A1}$, $V_{A2}$, $V_{A3}$, and $V_{A4}$, it is possible to reduce the influence of variations in the fat distribution within the trunk area.

In this state, the constant current IA is flowing between both arms and both legs, which are positioned at a distance from the trunk area, and thus almost all of the applied constant current IA passes through areas of low electrical resistance, or in other words, through areas aside from fat. Accordingly, the stated body impedance Zt calculated from the potential differences $V_{A1}$, $V_{A2}$, $V_{A3}$, and $V_{A4}$ measured using the constant current IA is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B the four pairs of electrodes are attached to the back area surface of the measurement subject with each pair disposed so as to follow the body axis direction, and with the four pairs arranged in the widthwise direction of the trunk area, in order to obtain the body impedance of the surface layer area on the back area side of the trunk area. In other words, as shown in. FIG. 1B a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

In this state, a constant current $I_{B1}$ that passes through the back area locally is applied to the measurement subject using the pair of electrodes $EIa_{B1}$ and $EIb_{B1}$, and a constant current $I_{B2}$ that passes through the back area locally is applied to the measurement subject using the pair of electrodes $EIa_{B2}$ and $EIb_{B2}$. While the constant currents $I_{B1}$ and $I_{B2}$ are applied, a potential difference $V_{B1}$ is detected using the pair of electrodes $EVa_{B1}$ and $EVb_{B1}$ attached to the back area surface, and a potential difference $V_{B2}$ is detected using the pair of electrodes $EVa_{B2}$ and $EVb_{B2}$ attached to the back area surface. Here, the current values of the two constant currents $I_{B1}$ and $I_{B2}$ applied to the measurement subject are set to the same value.

A body impedance Zs of the surface layer area on the back area side of the trunk area is calculated form the potential differences $V_{B1}$ and $V_{B2}$ calculated in this manner. Note that if the body impedance Zs is found at this time by calculating the average value of the two stated potential differences $V_{B1}$ and $V_{B2}$, it is possible to reduce the influence of variations in the fat distribution within the surface layer area in the back area of the trunk area. Note that potential differences can also be measured in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area, and thus almost all of both the applied constant currents $I_{B1}$ and $I_{B2}$ pass through the surface layer area of the back area. Accordingly, the stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs obtained in this manner will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \quad \text{Formula (1)}$$

Here, the trunk area cross-sectional area St can be calculated using the circumferential length of the trunk area (the so-called waist length), the width of the trunk area, the depth of the trunk area, and so on. For example, in the case where the trunk area cross-sectional area St is to be calculated from the width and depth of the trunk area, assuming that the width of the trunk area is taken as 2×a and the depth of the trunk area is taken as 2×b, and because the trunk area has a generally oval cross-sectional shape, the trunk area cross-sectional area St can be approximated through the following Formula (2).

$$St = \pi \times a \times b \quad \text{Formula (2)}$$

However, the trunk area cross-sectional area St approximated through the above Formula (2) is highly likely to contain a significant degree of error, and it is thus preferable to find a more accurate trunk area cross-sectional area St by multiplying that trunk area cross-sectional area St by a coefficient α for reducing error. This coefficient α is obtained, for example, by finding the optimum value for a that fulfills St'=α×π×a×b, from the relationship between the stated a and b and a trunk area cross-sectional area St' obtained from a sample of a large number of X-ray CT images.

Accordingly, the stated Formula (2) can approximate with a lower degree of error through the following Formula (3) by using the coefficient α.

$$St = \alpha \times \pi \times a \times b \quad \text{Formula (3)}$$

Note that it is preferable to optimize the coefficient α multiplied for correction as described above as appropriate in accordance with information such as the measurement subject's sex, age, height, weight, and so on (hereinafter, this information will be referred to collectively as "measurement subject information"). In other words, the trunk area cross-sectional area St can be approximated with a higher degree of accuracy by changing the value of the stated coefficient α in accordance with the TO measurement subject information.

As described above, the non-fat cross-sectional area Sa can be calculated based on the body impedance Zt of the entire trunk area. However, the non-fat cross-sectional area Sa cannot be accurately calculated using only the body impedance Zt of the entire trunk area. That is, the non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times a \times (1/Zt) \quad \text{Formula (4)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. In other words, the optimum value for β that fulfils Sa'=β×a×(1/Zt) can be found from the relationship between a non-fat cross-sectional area Sa' obtained from a sample of a large number of X-ray CT images, the body impedance Zt of the entire trunk area of the measurement subject imaged by the X-ray CT, and the stated a.

Note that it is preferable for the stated coefficient β to be optimized as appropriate in accordance with the measurement subject information, in the same manner as the coefficient α mentioned above. In other words, the non-fat cross-sectional area Sa can be approximated with a higher degree of accuracy by changing the value of the stated coefficient β in accordance with the measurement subject information.

Furthermore, as described above, the subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. That is, the subcutaneous fat cross-sectional area Sb tends to be proportional to the size of the trunk area, and thus it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times a \times Zs \qquad \text{Formula (5)}$$

Here, a is a value that is half the width of the trunk area, as mentioned above, and is thus a value that is related to the size of the trunk area. However, the values related to the size of the trunk area are not limited to a, and, for example, a×b may be used in order to reflect the width and the depth of the trunk area, trunk area cross-sectional area St may be used, the circumferential length of the trunk area may be used, and so on.

Meanwhile, γ represents a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient α or the coefficient β. In other words, the optimum value for γ that fulfils Sb'=γ×a×Zs can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated a.

Note that it is preferable for the stated coefficient γ to be optimized as appropriate in accordance with the measurement subject information, in the same manner as the coefficient α and the coefficient β mentioned above. In other words, the subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area; more specifically, the visceral fat cross-sectional area Sx is calculated based on the following Formula (6) by substituting the stated Formula (3) through Formula (5) in the stated Formula (1).

$$Sx = \alpha \times \pi \times a \times b - \beta \times a \times (1/Zt) - \gamma \times a \times Zs \qquad \text{Formula (6)}$$

Functional Block of Body Fat Measurement Device

Figure 2:
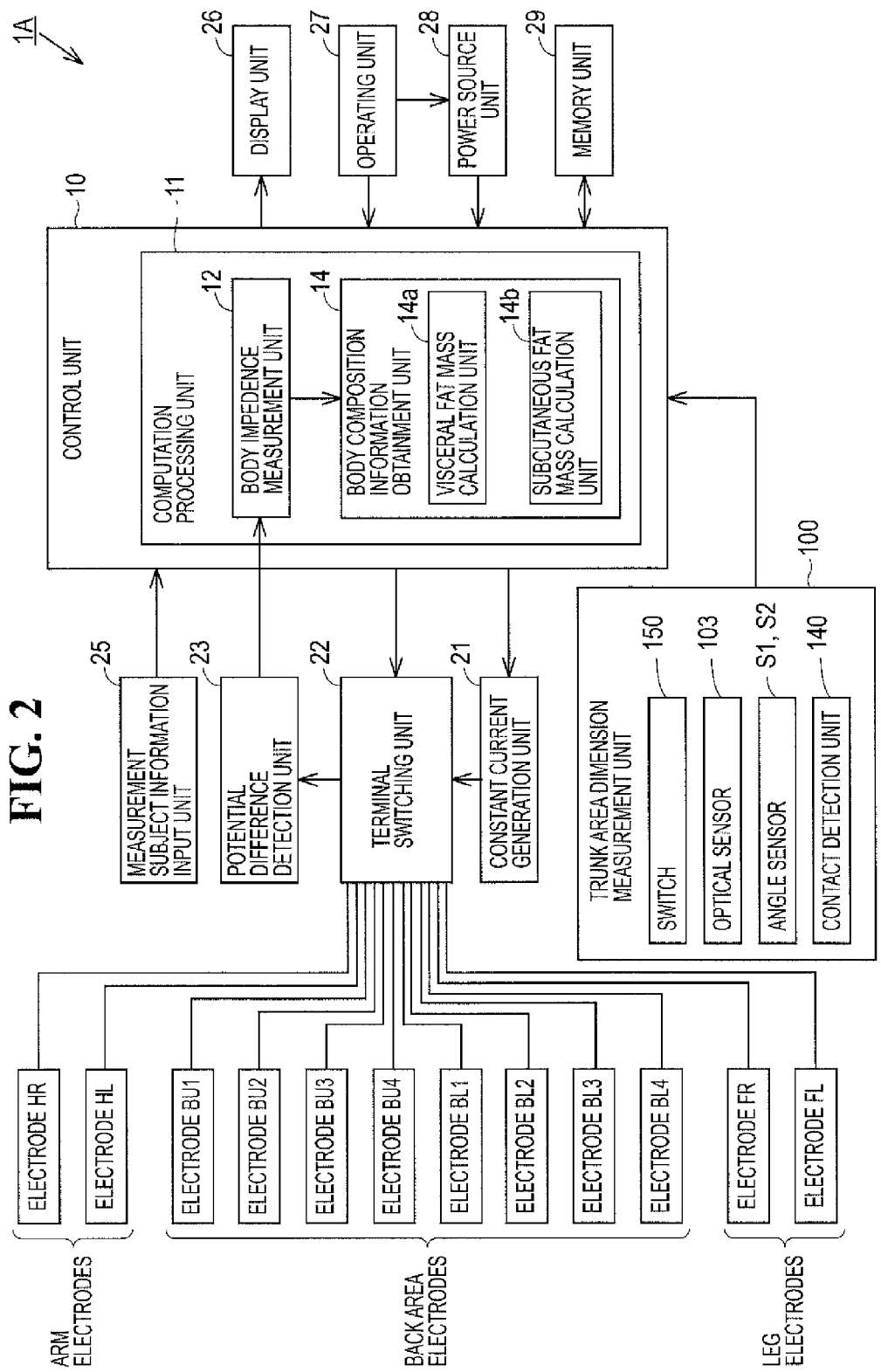
FIG. 2 is a diagram illustrating the functional block configuration of the body fat measurement device according to an embodiment of the present invention

FIG. 2 is a diagram illustrating the functional block configuration of the body fat measurement device according to the present embodiment. Next, the functional block configuration of the body fat measurement device according to the present embodiment will be described with reference to FIG. 2.

As shown in FIG. 2, a body fat measurement device 1A according to the present embodiment primarily includes: a control unit 10; a constant current generation unit 21; a terminal switching unit 22; a potential difference detection unit 23; a measurement subject information input unit 25; a trunk area dimension measurement unit 100; a display unit 26; an operating unit 27; a power source unit 28; a memory unit 29; and multiple electrodes HR, HL, BU1-BU4, BL1-BL4, FR, and FL that are fitted to the body of the measurement subject. The control unit 10 includes a computation processing unit 11, and the computation processing unit 11 has a body impedance measurement unit 12, and a body composition information obtainment unit 14.

The trunk area dimension measurement unit 100 is for measuring a trunk area width 2×a and a trunk area depth 2×b, and measures the trunk area width 2×a and the trunk area depth 2×b by obtaining information from a measurement start switch 150 for starting the measurement, an optical sensor 103, angle sensors S1 and S2, and a contact detection unit 140. The configuration of the device will be described later.

The control unit 10 is configured of, for example, a CPU (Central Processor Unit), and is a unit for controlling the body fat measurement device 1A as a whole. Specifically, the control unit 10 outputs instructions to the various aforementioned functional blocks, accepts inputs of various types of information from the various aforementioned functional blocks, performs various types of computation processes based on the various types of information accepted, and so on. The various types of computation processes are carried out by the stated computation processing unit 11 provided in the control unit 10.

The aforementioned multiple electrodes include: arm electrodes HR and HL serving as upper limb electrodes placed in contact with surfaces of the upper limbs of the measurement subject; back area electrodes BU1-BU4 and BL1-BL4 placed in contact with the back area surface of the measurement subject; and leg electrodes FR and FL serving as lower limb electrodes placed in contact with the surfaces of the lower limbs of the measurement subject. Of these, the arm electrodes HR and HL are placed in contact with the palms of the measurement subject's hands, and the leg electrodes FR and FL are placed in contact with the soles of the measurement subject's feet. Meanwhile, as shown in FIG. 1A and FIG. 1B the back area electrodes BU1-BU4 and BL1-BL4 are arranged in rows and placed in contact with the back area surface of the measurement subject. Note that the arm electrodes HR and HL, back area electrodes BU1-BU4 and BL1-BU4, and leg electrodes FR and FL are all electrically connected to the terminal switching unit 22 described above.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. Through this, the electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes. In other words, by the terminal switching unit 22 operating based on instructions inputted from the control unit 10, electrodes from among the stated multiple electrodes HR and HL, BU1-BU4 and BL1-BL4, FR and FL function as the respective electrodes $EIa_{A1}$, $EIa_{A2}$, $EVa_{A1}$, $EVb_{A1}$, $EVa_{A2}$, $EVb_{A2}$, $EVa_{A3}$, $EVb_{A3}$, $EVa_{A4}$, $EVb_{A4}$, $EIb_{A1}$, and $EIb_{A2}$, shown in FIG. 1(A) and the respective electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$ shown in FIG. 1(B).

The constant current generation unit 21 generates a constant current based on an instruction inputted from the control unit 10, and supplies the generated constant current to the stated constant current application electrodes via the terminal switching unit 22. A high-frequency current (for example, 50 kHz, 500 μA) that can be used effectively for measuring body composition information is selected as the constant current generated by the constant current generation unit 21. Through this, the constant current can be applied to the measurement subject via the constant current application electrodes.

The potential difference detection unit 23 detects a potential difference between the electrodes electrically connected to the potential difference detection unit 23 by the terminal switching unit 22 (that is, the potential difference detection electrodes), and outputs the detected potential difference to the control unit 10. Through this, the potential difference between the potential difference detection electrodes is detected in a state in which the aforementioned constant current is applied to the measurement subject.

Various types of information obtained from the trunk area dimension measurement unit 100 are sent to the control unit 10 and are subjected to computation processes by the control unit 10, and the trunk area width 2×a and the trunk area depth 2×b are calculated and are outputted to the body composition information obtainment unit 14.

The measurement subject information input unit 25 is a unit for obtaining information regarding the measurement subject used in computation processes carried out by the computation processing unit 11, and is configured of, for example, keys and the like that can be depressed by the measurement subject. Here, the measurement subject information includes at least one of the sex, age, height, weight, and so on of the measurement subject, as mentioned above. The measurement subject information input unit 25 accepts the input of measurement subject information, and outputs the accepted measurement subject information to the control unit 10. Note that the measurement subject information input unit 25 is not absolutely necessary in the configuration of the present invention, and whether or not to provide the measurement subject information input unit 25 can be determined based on whether or not it is necessary to use the measurement subject information in the computation processes performed by the computation processing unit 11.

The computation processing unit 11 includes the body impedance measurement unit 12, the body shape information measurement unit 13, and the body composition information obtainment unit 14, as mentioned above. Moreover, the body composition information obtainment unit 14 includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14.

The body composition information obtainment unit 14 calculates and obtains the body composition information based on the body impedance inputted from the body impedance measurement unit 12, the width and depth of the trunk area obtained from the trunk area dimension measurement unit 100, and in some cases, the measurement subject information inputted from the measurement subject information input unit 25 as well. More specifically, the visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14 as mentioned above. More specifically, the visceral fat mass calculated by the visceral fat mass calculation unit 14a and the subcutaneous fat mass calculated by the subcutaneous fat mass calculation unit 14b are displayed in the display unit 26 based on signals outputted from the control unit 10. Here, in the body fat measurement device 1A according to the present embodiment, the visceral fat mass is displayed as, for example, the visceral fat cross-sectional area, and the subcutaneous fat mass is displayed as, for example, the subcutaneous fat cross-sectional area.

The operating unit 27 is a unit through which the measurement subject inputs commands to the body fat measurement device 1A, and is configured of, for example, buttons and the like that can be depressed by the measurement subject. Note that the operating unit 27 includes various types of operation buttons such as a power button, a measure button, and so on.

The power source unit 28 is a unit for supplying electrical power to the control unit 10, and uses an internal power source such as a battery, an external power source such as an AC outlet, or the like.

The memory unit 29 is configured of, for example, a random access memory (RAM) or a read-only memory (ROM), and is a unit for storing various types of data, programs, and the like for the body fat measurement device 1A. The memory unit 29 stores, for example, the aforementioned measurement subject information, the calculated body composition information, a body composition information measurement program for executing a body composition information measurement process (mentioned later), and so on.

Trunk Area Dimension Measurement Device 100

Figure 5:
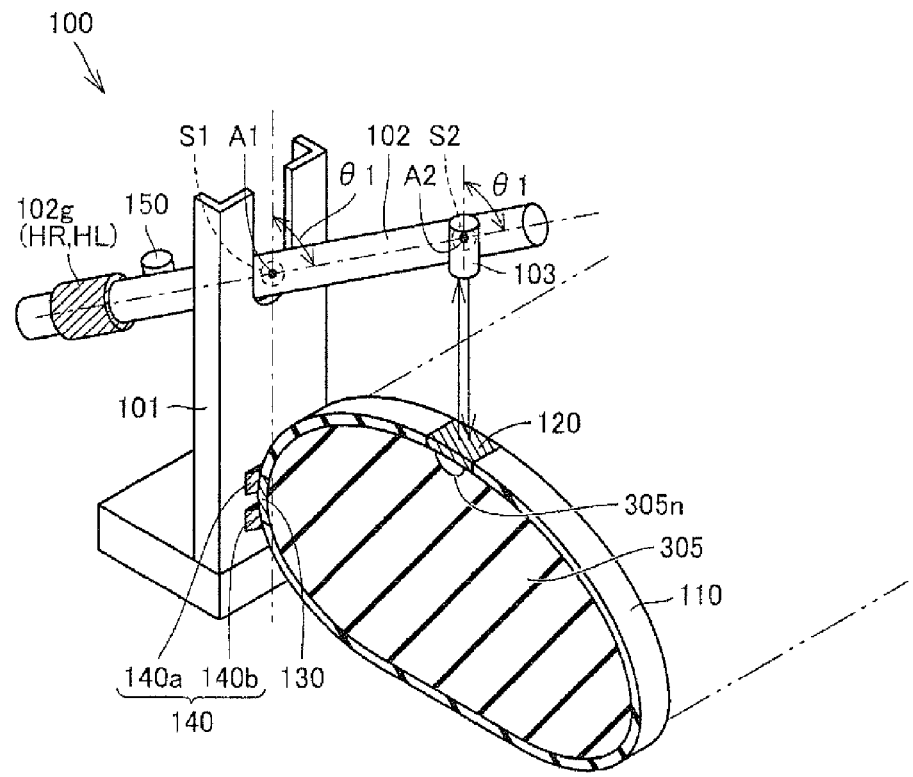
FIG. 5 is a perspective view illustrating a specific configuration of a trunk area dimension measurement device according an embodiment of the present invention.
Figure 6:
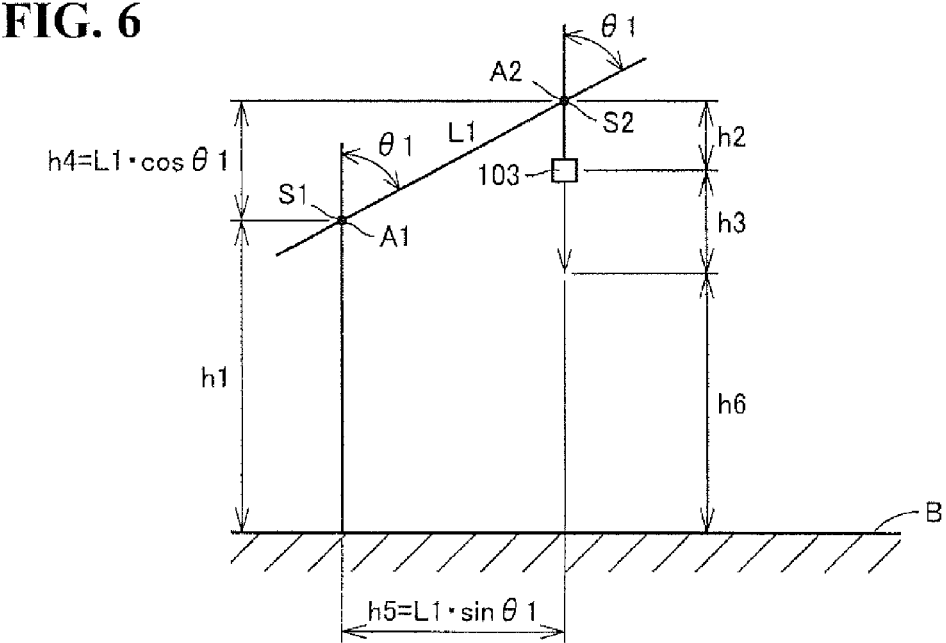
FIG. 6 is a schematic diagram illustrating a measurement method performed by a trunk area dimension measurement device according an embodiment of the present invention.

Next, details of the structure of the trunk area dimension measurement device 100 serving as a trunk area dimension measurement unit will be described with reference to FIGS. 3 to 6. Note that FIG. 3 is a cross-sectional view illustrating a schematic configuration of the trunk area dimension measurement device 100, FIG. 4 is a cross-sectional view illustrating details of the structure of a contact detection unit 140 and a contact portion 130 that are adopted into the trunk area dimension measurement device 100, FIG. 5 is a perspective view illustrating a specific configuration of the trunk area dimension measurement device 100, and FIG. 6 is a schematic diagram illustrating a measurement method performed by the trunk area dimension measurement device 100.

Figure 3:
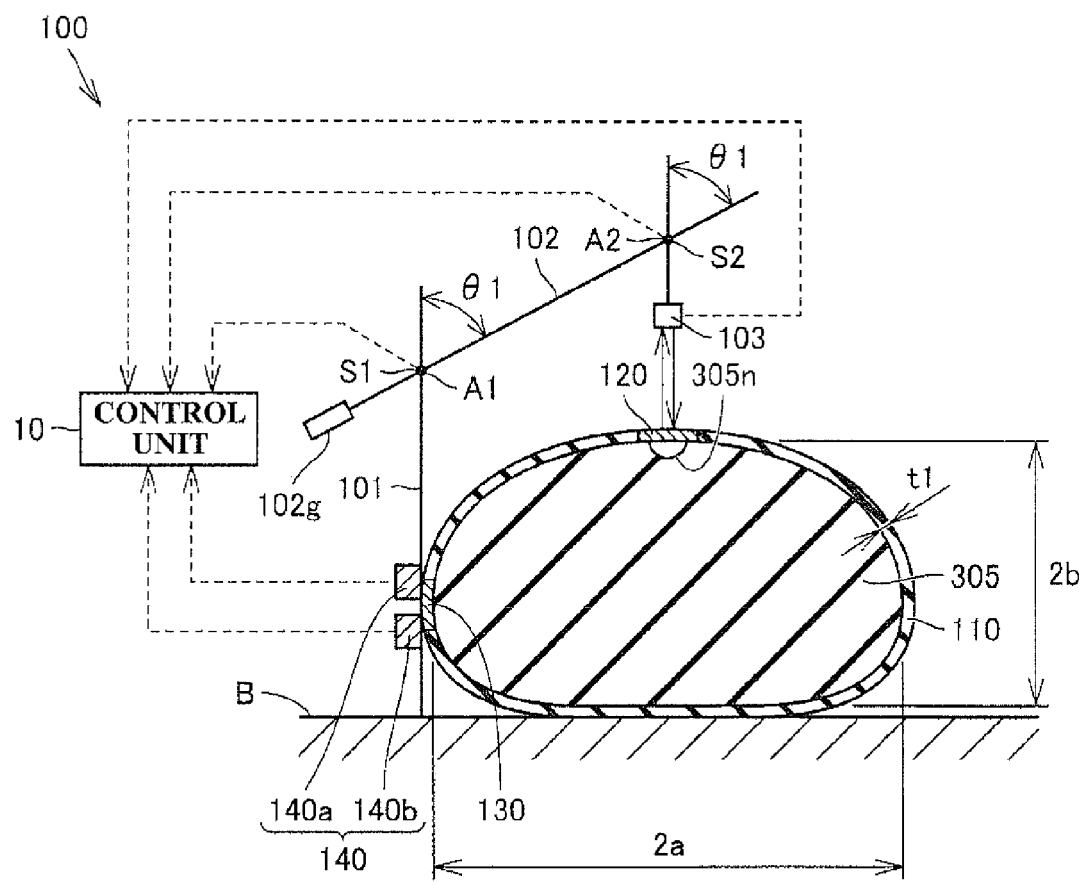
FIG. 3 is a cross-sectional view illustrating a schematic configuration of a trunk area dimension measurement device according an embodiment of the present invention.
Figure 4:
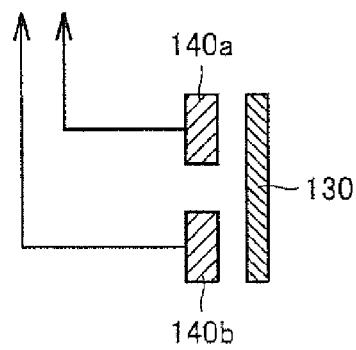
FIG. 4 is a cross-sectional view illustrating details of the structure of a contact detection unit and a contact potion that are adopted into a trunk area dimension measurement device according to an embodiment of the present invention.

Referring to FIGS. 3 and 4, the trunk area dimension measurement device 100 is a trunk area dimension measurement device for measuring a trunk area width 2×a and a trunk area depth 2×b of a measurement subject who is lying face-up. The trunk area dimension measurement device 100 has a light reflection portion 120 to be placed at a position of a navel 305n of the measurement subject, a contact portion 130 to be placed on one side surface of a measurement subject's trunk area 305 (in FIG. 3, a right flank), a support column 101 that has a contact detection unit 140 placed on the side surface of the measurement subject's trunk area 305 and detecting the contact with the contact portion 130 and that extends in a vertical direction, a measurement bar 102 that is supported pivotably about a first support point A1 vertically with respect to the support column 101 and that extends above the measurement subject's trunk area 305, and an optical sensor 103 that is held by the measurement bar 102 positioned above the measurement subject's trunk area and that is held pivotably about a second support point A2 so as to hang down in a gravity direction. In the present embodiment, although the case where the first support point A1 is positioned vertically above the contact detection unit 140 is shown in FIG. 3, the present invention is not limited to this configuration.

A grip 102g to be held by the measurement subject is provided on an end side opposite to the other end side of the measurement bar 102 on which the optical sensor 103 is provided with the first support point A1 of the measurement bar 102 interposed therebetween. Also, the grip may be provided with the arm electrodes HR and HL. A measurement start switch 150 that sends signals for starting the measurement performed by the trunk area dimension measurement device 100 to the control unit 10 is provided on the measurement bar 102 in the vicinity of the grip 102g. Note that the measurement start switch 150 is not necessarily provided on the measurement bar 102, and may be operated by a wireless remote controller, a wired remote controller, or the like.

A first angle sensor S1 for measuring an intersection angle θ1 of the support column 101 and the measurement bar 102 (inclination angle of the measurement bar 102 with respect to the vertical direction) is provided at the first support point A1, and a second angle sensor S2 for measuring an intersection angle θ2 of the measurement bar 102 and the optical axis direction of the optical sensor 103 (inclination angle of the measurement bar 102 with respect to the vertical direction) is provided at the second support point A2. In the present embodiment, since the support column 101 extends in the vertical direction and the optical axis direction of the optical sensor 103 extends in the vertical direction, the intersection angle θ1 and the intersection angle θ2 are the same. Thus, the angle sensor need only be provided at either one of the first support point A1 and the second support point A2.

Although in the present embodiment, a configuration is adopted in which the light reflection portion 120 and the contact portion 130 are provided on a belt member 110 to be fitted around the measurement subject's trunk area 305, the configuration is not limited thereto. For example, an adhesive sheet may be attached to the reverse surfaces of the light reflection portion 120 and the contact portion 130 to directly affix the light reflection portion 120 and the contact portion 130 to the measurement subject's trunk area 305.

Moreover, as shown in FIG. 4, a configuration is adopted in which a conductive plate member is used for the contact portion 130 and the first contact detection unit 140a and the second contact detection unit 140b are used for the contact detection unit 140 so that electrification is ensured between the first contact detection unit 140a and the second contact detection unit 140b by the contact portion 130 making contact with the first contact detection unit 140a and the second contact detection unit 140b.

Accordingly, when the contact portion 130 is in contact with the contact detection unit 140, information of the current flow is sent to the control unit 10, and when the contact portion 130 is not in contact with the contact detection unit 140, information of no current flow is sent to the control unit 10.

Note that the configuration shown in FIG. 4 is an example, and it is possible to adopt another mechanism as long as the structure has a mechanism detecting the contact or the non-contact.

Measurement Procedure

Next, a procedure for measuring a trunk area width 2×a and a trunk area depth 2×b of the measurement subject using the trunk area dimension measurement device 100 is described with reference to FIGS. 3 and 6. When the measurement subject is in a position lying face-up, the contact portion 130 is positioned to be in contact with the contact detection unit 140. When the contact portion 130 is not contact with the contact detection unit 140, it is not possible to start the measurement.

The measurement subject holds the grip 102g and adjusts the inclination angle of the measurement bar 102 so that the optical sensor 103 is positioned right above the light reflection portion 120. Light emitted from the optical sensor 103 returns to the optical sensor 103 because the optical sensor 103 is positioned right above the light reflection portion 120, and thus a distance h3 between the optical sensor 103 and the light reflection portion 120 can be measured.

The measurement subject confirms that the optical sensor 103 is positioned right above the light reflection portion 120 and presses the measurement start switch 150. Accordingly, the measurement performed by the trunk area dimension measurement device 100 is started.

As shown in FIG. 6, a distance h1 from a base position B at which the measurement subject lies face-up to the first support point A1, a length L1 from the first support point A1 to the second support point A2, and a distance h2 from the second support point A2 to the optical sensor 103 are inputted into the control unit 10 in advance.

Therefore, a vertical length h4 from the first support point A1 to the second support point A2 is calculated by the trunk area dimension measurement device 100 measuring θ1 (or θ2) and the distance h3 based on the following Formula (7).

$$h4 = L1 \times \cos\theta 1 \qquad \text{Formula (7)}$$

Moreover, a horizontal length h5 from the first support point A1 to the second support point A2 is calculated based on the following Formula (8).

$$h5 = L1 \times \sin\theta 1 \qquad \text{Formula (8)}$$

As a result, in the case where the belt member 110 is used, the measurement subject's trunk area width 2×a is calculated through the following Formula (9) where the thickness of the belt is t.

$$2 \times a = 2 \times (h5 - t) \qquad \text{Formula (9)}$$

Moreover, the measurement subject's trunk area depth 2×b is calculated through the following Formula (10).

$$2 \times b = [(h1 + h4) - (h2 + h3) - 2 \times t] \qquad \text{Formula (10)}$$

The trunk area width 2×a and the trunk area depth 2×b of the measurement subject measured by the trunk area dimension measurement device 100 are used in the control unit 10 to calculate the trunk area cross-sectional area St through the stated Formulae (2) or (3), the subcutaneous fat cross-sectional area Sb through Formula (5), and the visceral fat cross-sectional area Sx through Formula (6).

According to the trunk area dimension measurement device 100 in the present embodiment, the device configuration can be simplified because of the configuration in which the support column 100 and the measurement bar 102 are used. Moreover, it is possible to reduce the size of the trunk area dimension measurement device 100 because the configuration in which the trunk area dimension measurement device 100 is placed only on one side of the measurement subject's sides is adopted.

Furthermore, since the measurement bar 102 pivots about only one location, i.e. the first support point A1, with respect to the support column 101, the measurement subject him or herself can easily operate the measurement bar 102, a caregiver is not required, and the measurement can be performed by the measurement subject him or herself.

Accordingly, in the trunk area dimension measurement device 100 and the body fat measurement device employing the trunk area dimension measurement device, it is possible to avoid scaling up the device, to simplify the structure, and also suppress an increase in the cost.

Note that although the configuration is adopted in which the contact with the support column 101 is detected by providing the contact portion 130 at a side of the measurement subject's trunk area (flank) in the above embodiment, it is also possible to adopt the configuration in which the contact detection unit 140 directly makes contact with a side of the measurement subject's trunk area (flank).

Moreover, although in the present embodiment, the configuration is employed in which the support column 101 extends in the vertical direction and the first support point A1 is provided at a position substantially vertically above the contact detection unit 140, the position of the first support point A1 may be located on the side of a trunk area side (right side in FIG. 3), or at the outside of the trunk area (left side in FIG. 3). Since the amount of positional shift of the first support point A1 in the horizontal direction with respect to the contact detection unit 140 is stored in the control unit 10 in advance, it is possible to measure the trunk area width 2×a and the trunk area depth 2×b of the measurement subject based on information on the inclination angle of the measurement bar 102 with respect to the vertical direction that is obtained from the angle sensors S1 and S2.

In addition, although the aforementioned embodiment of the present invention describes an example in which the computation processing is configured so as to calculate the visceral fat cross-sectional area as the visceral fat mass and the subcutaneous fat cross-sectional area as the subcutaneous fat mass, the computation processing may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

Note that although the aforementioned embodiment describes the case where the distance h3 is determined using the optical sensor 103 and the light reflection portion 120 provided on the belt member 110 wrapped around the measurement subject's trunk area, the present invention is not limited thereto. For example, if a range sensor (product number GP2D12 manufactured by Sharp Corp. or the like, for example) in which an infrared emitting diode is used is used instead of the optical sensor 103, the light reflection portion 120 is not required. Moreover, if an on/off switch that functions based on the contact of the measurement subject's trunk area is provided on the support column 101 instead of the contact portion 130 and the contact detection unit 140, the belt member 110 is not required.

In the case where the distance h3 is determined using the range sensor, it is preferable that a position at which the distance is measured by the range sensor is indicated clearly by using a laser pointer or the like so that the measurement subject him or herself can recognize the position for measuring the abdominal area. Note that in the case where the distance is measured using the optical sensor 103 and the light reflection portion 120, the measurement is automatically completed when light from the light reflection portion 120 returns, and in the case where the range sensor is used without using the light reflection portion, the measurement subject manually measures the distance.

Although an embodiment of the present invention has been described above, the embodiment disclosed herein is to be considered in all respects as illustrative and not restrictive. The scope of the present invention is defined by the claims, and all changes that come within the meaning and range of equivalency of the claims are intended to be embraced therein.

REFERENCE SIGNS LIST 1A body fat measurement device
10 control unit
11 computation processing unit
12 body impedance measurement unit
13 body shape information measurement unit
14 body composition information obtainment unit
14a visceral fat mass calculation unit
14b subcutaneous fat mass calculation unit
21 constant current generation unit
22 terminal switching unit
23 potential difference detection unit
24A trunk area width detection unit
24B trunk area depth detection unit
25 measurement subject information input unit
26 display unit
27 operating unit
28 power source unit
29 memory unit
100 trunk area dimension measurement device (trunk area dimension measurement unit)
101 support column
102 measurement bar
102g grip
103 optical sensor
110 belt member
120 light reflection portion
130 contact portion
140 contact detection unit
140a first contact detection unit
140b second contact detection unit
150 measurement start switch
305 trunk area
305n navel
A1 first support point
A2 second support point
S1 first angle sensor
S2 second angle sensor

The invention claimed is:

1. A body fat measurement device for measuring a measurement subject who is laying face-up, the body fat measurement device comprising:
   a trunk area dimension measurement device configured to measure a trunk area width and a trunk area depth of the measurement subject, the trunk area dimension measurement device includes:
      a support column to be placed on a side surface of the trunk area of the measurement subject;
      a measurement bar that is supported pivotably about a first support point vertically with respect to the support column and that extends above the trunk area of the measurement subject;
      a distance sensor that is held by the measurement bar positioned above the trunk area of the measurement subject and that is held pivotably about a second support point so as to hang down in a gravity direction, the distance sensor being an optical sensor;
      an angle sensor that is provided at either one of the first support point and the second support point; and
      a light reflection portion disposed at a position of a navel of the measurement subject;
      a contact detection unit that is provided on the support column, the contact detection unit being configured to detect contact with the trunk area; and
      a control unit configured to process information on an inclination angle of the measurement bar with respect to a vertical direction that is obtained from the angle sensor, information that is obtained from the distance sensor, and information that is obtained from the contact detection unit with respect to the contact with the trunk area,
   the control unit being configured to measure only (i) the distance information, which is a distance between the optical sensor and the light reflection portion, and (ii) the inclination angle information of the measurement bar with respect to the vertical direction obtained from the angle sensor, in order to calculate the trunk area width and trunk area depth of the measurement subject
   the control unit calculating the trunk area width $2 \times \alpha$ based on:

$$2 \times \alpha = 2 \times (h5-t)$$

wherein h5 is a horizontal length from a first support point to a second support point, and t is a thickness of a belt wrapped around the trunk area of the measurement subject.

2. A body fat measurement device for measuring a measurement subject who is laying face-up, the body fat measurement device comprising:
   a trunk area dimension measurement device configured to measure a trunk area width and a trunk area depth of the measurement subject, the trunk area dimension measurement device includes:
      a support column to be placed on a side surface of the trunk area of the measurement subject;
      a measurement bar that is supported pivotably about a first support point vertically with respect to the support column and that extends above the trunk area of the measurement subject;
      a distance sensor that is held by the measurement bar positioned above the trunk area of the measurement subject and that is held pivotably about a second support point so as to hang down in a gravity direction, the distance sensor being an optical sensor;
      an angle sensor that is provided at either one of the first support point and the second support point; and
      a light reflection portion disposed at a position of a navel of the measurement subject;
      a contact detection unit that is provided on the support column, the contact detection unit being configured to detect contact with the trunk area; and
      a control unit configured to process information on an inclination angle of the measurement bar with respect to a vertical direction that is obtained from the angle sensor, information that is obtained from the distance sensor, and information that is obtained from the contact detection unit with respect to the contact with the trunk area,
   the control unit being configured to measure only (i) the distance information, which is a distance between the optical sensor and the light reflection portion, and (ii) the inclination angle information of the measurement bar with respect to the vertical direction obtained from the angle sensor, in order to calculate the trunk area width and trunk area depth of the measurement subject
   the control unit calculating the trunk area depth $2 \times b$ based on:

$$2 \times b = [(h1+h4)-(h2+h3)-2 \times t]$$

wherein h1 is a length from a base position to a first support point, h2 is a length from a second support point to the optical sensor, h3 is a length from the optical sensor to the light reflection portion, h4 is a vertical length from the first support point to the second support point, and t is a thickness of a belt wrapped around the trunk area of the measurement subject.

3. The body fat measurement device according to claim 1, wherein a contact portion is placed on one side surface of the measurement subject's trunk area, and
   the contact detection unit sends:
      information of a current flow to the control unit when the contact portion is in contact with the contact detection unit, and
      information of no current flow to the control unit when the contact portion is not in contact with the contact detection unit.

4. The body fat dimension measurement device according to claim 3, wherein the light reflection portion and the contact portion are provided on a belt member to be fitted around the trunk area of the measurement subject.

5. The body fat dimension measurement device according to claim 1, further comprising:
   a grip portion on a side opposite to the side on which the optical sensor is provided with the first support point of the measurement bar interposed therebetween,
   wherein a measurement start switch that sends a signal for starting a measurement performed by the trunk area dimension measurement device to the control unit is provided in the vicinity of the grip portion.

6. The body fat measurement device according to claim 2, wherein a contact portion is placed on one side surface of the measurement subject's trunk area, and
   the contact detection unit sends:
      information of a current flow to the control unit when the contact portion is in contact with the contact detection unit, and
      information of no current flow to the control unit when the contact portion is not in contact with the contact detection unit.

7. The body fat dimension measurement device according to claim 6, wherein the light reflection portion and the contact portion are provided on a belt member to be fitted around the trunk area of the measurement subject.

8. The body fat dimension measurement device according to claim 2, further comprising:
   a grip portion on a side opposite to the side on which the optical sensor is provided with the first support point of the measurement bar interposed therebetween,
   wherein a measurement start switch that sends a signal for starting a measurement performed by the trunk area dimension measurement device to the control unit is provided in the vicinity of the grip portion.

* * * * *